United States Patent [19]
Mauric et al.

[11] Patent Number: 4,458,045
[45] Date of Patent: Jul. 3, 1984

[54] FLAMEPROOFED ORGANIC MATERIALS

[75] Inventors: Claudine Mauric, Basel; Rainer Wolf, Allschwil, both of Switzerland

[73] Assignee: Sandoz Ltd., Basel, Switzerland

[21] Appl. No.: 476,767

[22] Filed: Mar. 18, 1983

Related U.S. Application Data

[63] Continuation-in-part of Ser. No. 121,205, Feb. 13, 1980, Pat. No. 4,388,431.

[30] Foreign Application Priority Data

Feb. 14, 1979 [CH] Switzerland .......................... 1461/79
Feb. 23, 1979 [CH] Switzerland .......................... 1839/79

[51] Int. Cl.$^3$ ........................... C08K 5/52; C08K 5/53
[52] U.S. Cl. .................................... 524/119; 524/710; 523/351
[58] Field of Search ............... 524/119, 121, 122, 125, 524/710; 523/351; 260/927 R

[56] References Cited

U.S. PATENT DOCUMENTS 2,540,146 12/1951 Stober ................................. 523/351
3,049,545 8/1962 Birum ................................. 524/121
3,970,635 7/1976 Lawton et al. ..................... 524/119
4,160,795 7/1979 Albright et al. ................. 260/927 R
4,268,459 5/1981 Hoffman ......................... 260/927 R Primary Examiner—John Kight, III
Assistant Examiner—Kriellion Morgan
Attorney, Agent, or Firm—Gerald D. Sharkin; Richard E. Vila; Thomas C. Doyle

[57] ABSTRACT

A group of diphosphonic acid tetra-esters and phosphonic or thiophosphonic acid 0,0,0-triesters containing dioxaphosphorinane rings are useful as flame retardants for polymeric organic materials, particularly polyesters. The compounds, some of which are novel, are prepared by reaction of the corresponding phosphites with peroxy compounds or with sulphur.

18 Claims, No Drawings

FLAMEPROOFED ORGANIC MATERIALS

This application is a continuation-in-part of application Ser. No. 121 205, filed on Feb. 13, 1980, now U.S. Pat. No. 4,388,431.

This invention relates to flameproofed polymeric organic materials containing, as flameproofing agents, organic phosphorus compounds.

The invention provides flameproofed polymeric organic materials containing a compound of formula I

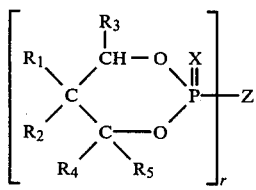

in which
$R_1$ and $R_2$ are independently hydrogen, $C_{1-4}$alkyl or phenyl; or $R_1$ and $R_2$ together with the carbon atom to which they are attached form a cyclohexylidene or cyclohexenylidene ring,
$R_3$ and $R_4$ are independently hydrogen or $C_{1-4}$alkyl,
$R_5$ is hydrogen or methyl,
provided that when $R_1$ and $R_2$ together with the carbon atom to which they are attached form a ring, then $R_3$, $R_4$ and $R_5$ are all hydrogen,
Z is a group $Z_a$ or $Z_b$ as defined below,
X is oxygen when Z is $Z_a$ and oxygen or sulphur when Z is $Z_b$,
r is 2 when Z is $Z_a$ and 2, 3 or 4 when Z is $Z_b$,
$Z_a$ is methylene, ethylene, phenylethylene, $C_{3-12}$ alkylene unsubstituted or substituted by up to 2 groups selected from phenyl or phenoxy, $C_{4-8}$ cycloalkylene unsubstituted or substituted by up to 2 groups selected from phenyl or phenoxy, $C_{4-12}$alkenylene in which the double bond is not in a terminal position, $C_{4-12}$alkynylene in which the triple bond is not in a terminal position, or a group

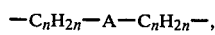

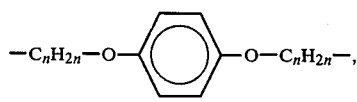

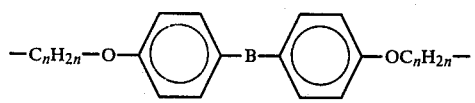

or

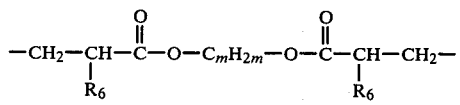

in which
A is $C_{4-8}$cycloalkylene or phenylene
B is

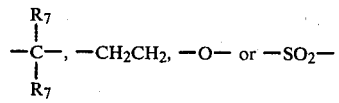

$R_6$ is hydrogen or methyl
$R_7$ is hydrogen or $C_{1-4}$alkyl
n is an integer from 2 to 5
and m is an integer from 2 to 12
and $Z_b$, when r=2 is

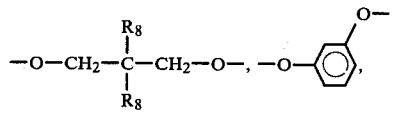

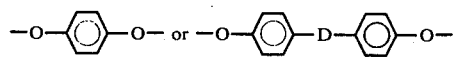

where $R_8$ is $C_{1-4}$alkyl, phenyl, $-CH_2Cl$ or $-CH_2Br$ and D is

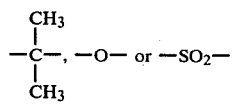

provided that when X is oxygen, $-Z_b-$ may not be

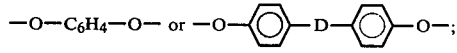

when r=3, is

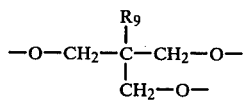

where $R_9$ is methyl or ethyl and when r=4, is

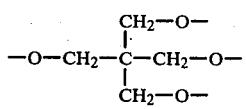

provided that when Z is $Z_b$, the polymeric organic material is other than cellulose or a cellulose derivative.

Where any symbol, for example n, $R_6$, $R_7$ or $R_8$, appears more than once in a formula, it is to be understood that it may have the same or different significances, unless otherwise stated. All groups capable of bearing substituents are unsubstituted unless otherwise stated. All alkylene groups, including $C_nH_{2n}$ and $C_mH_{2m}$, may, unless otherwise stated, be linear or branched, but are preferably linear.

Preferred significances of $R_1$ and $R_2$ are $R_1'$ and $R_2'$, where $R_1'$ and $R_2'$ are, independently, $C_{1-4}$alkyl or phenyl; more preferably they are $R_1''$ and $R_2''$ where $R_1''$ and $R_2''$ are, independently, $C_{1-4}$alkyl, even more preferably they are $R_1'''$ and $R_2'''$ where $R_1'''$ and $R_2'''$ are, independently, $C_{1-3}$alkyl, particularly methyl. When $R_1$ and $R_2$ are both alkyl, they are preferably the same.

$R_3$ is preferably $R_3'$ where $R_3'$ is hydrogen or $C_{1-3}$alkyl, more preferably $R_3''$ where $R_3''$ is hydrogen, n-propyl or isopropyl, particularly hydrogen.

$R_4$ is preferably hydrogen.

$R_5$ is preferably hydrogen.

$Z_a$ is preferably $Z_a'$ where $Z_a'$ is $C_{1-10}$alkylene, $C_{4-8}$cycloalkylene, 2-butenylene, 2-butynylene, $-C_nH_{2n}-A-C_nH_{2n}-$

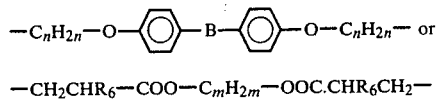

or $-CH_2CHR_6-COO-C_mH_{2m}-OOC.CHR_6CH_2-$ where A, B, $R_6$, n and m are as defined above.

More preferably $Z_a$ is $Z_a''$, that is, $C_{1-10}$alkylene, $C_{4-8}$cycloalkylene, 2-butenylene, 2-butynylene, 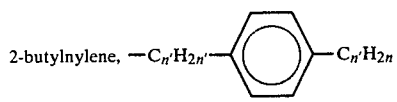

or $-CH_2CHR_6-COO-C_{m'}H_{2m'}-OOC-CHR_6CH_2-$ where n' is 2 or 3 and m' is 2 to 6.

Particularly preferred significances of $Z_a$ are given by $Z_a'''$ wherein $Z_a'''$ is $C_{1-10}$alkylene, $C_{6-8}$cycloalkylene, 2-butenylene or $-CH_2CHR_6-COO-C_{m''}H_{2m''}-OOC-CHR_6CH_2-$ where m'' is 2, 3 or 4.

$Z_a$ as $C_{1-10}$alkylene is preferably ethylene, propylene, butylene, hexylene or decylene, particularly ethylene, butylene, hexylene or decylene.

In $Z_a$, A is preferably p-phenylene or 1,4-cyclohexylene, particularly p-phenylene;

B is preferably

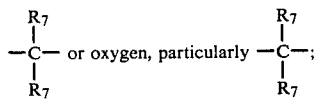

$R_7$ is preferably methyl or ethyl, particularly methyl;

n is preferably n', defined above, and both n's in the formula are preferably the same;

and m is preferably m', more preferably m'', defined above; r, when Z is $Z_b$ is preferably 2 or 3, more preferably 2.

When r is 2, $Z_b$ is preferably $Z_b'$ where $Z_b'$ is

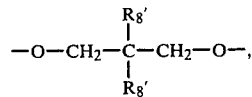

where $R_8'$ is $C_{1-4}$alkyl or phenyl, more preferably $Z_b''$ where $Z_b''$ is

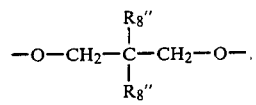

where $R_8''$ is $C_{1-4}$alkyl.

In $Z_b$, $R_8$ is preferably $R_8'$, defined above, more preferably $R_8''$, defined above, still more preferably $R_8'''$, that is, $C_{1-3}$alkyl, particularly methyl. Preferably both $R_8$'s are the same.

Of the compounds of formula I in which Z is $Z_a$, the compounds of formula $I_a'$

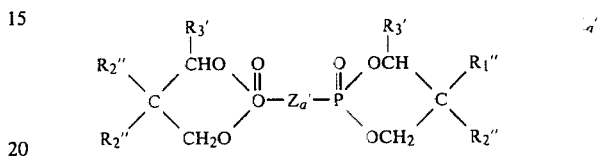

are preferred, particularly those of formula $I_a''$

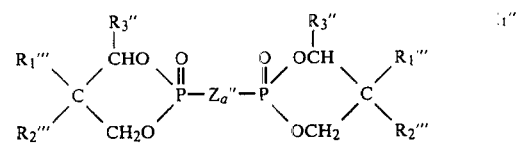

and especially those of formula $I_a'''$

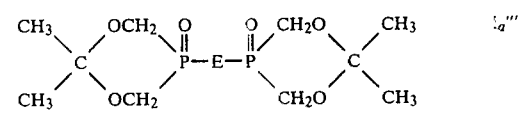

in which E is $C_{1-10}$alkylene.

Of the compounds of formula I in which Z is $Z_b$, the compounds of formula $I_b'$

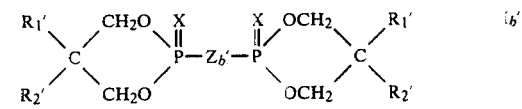

are preferred, particularly those of formula $I_b''$

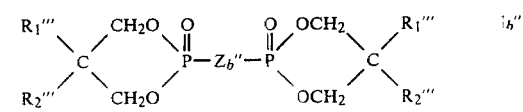

and especially the compound of formula $I_b'''$

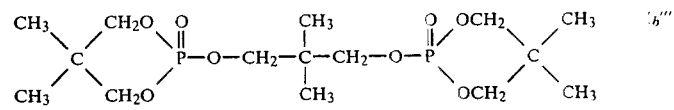

Compounds of formula II

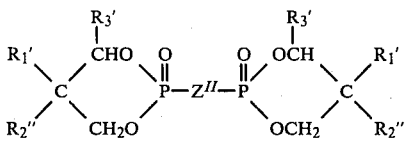 II in which
R$_1'$ is C$_{1-4}$alkyl or phenyl,
R$_2''$ is C$_{1-4}$alkyl,
R$_3'$ is hydrogen or C$_{1-3}$alkyl;
Z$^{II}$ is Z$_a^{II}$ or Z$_b^{II}$ where Z$_a^{II}$ is ethylene, propylene, C$_{5-10}$alkylene, C$_{6-8}$cycloalkylene, 2-butenylene,

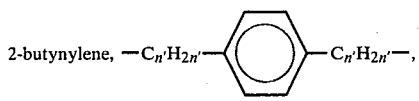

or —CH$_2$CHR$_6$—COO—C$_{m'}$H$_{2m'}$—OOC—CHR$_6$CH$_2$— where n' is 2 or 3, m' is 2 to 6 and R$_6$ is hydrogen or methyl,

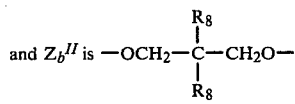

where R$_8$ is as defined above provided that, when both R$_1'$'s and both R$_2'''$'s are methyl and R$_3'$ is hydrogen, then at least one of the groups R$_8$ is other than methyl, are new, and constitute a further aspect of the present invention. Of these novel compounds, those in which Z$^{II}$ is Z$_a^{II}$ are preferred, preferably those in which Z$_a^{II}$ is alkylene, more preferably those in which Z$_a^{II}$ is linear C$_{5-10}$alkylene.

The invention also provides a process for the preparation of compounds of formula I in which X is oxygen characterised in that a compound of formula III

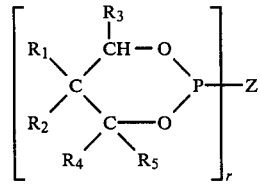 III in which R$_1$–R$_5$, r and Z are as defined above, is oxidized with a peroxy compound, preferably a per-acid. More particularly, the invention provides a process for the preparation of compounds of formula II characterised in that a compound of formula IV

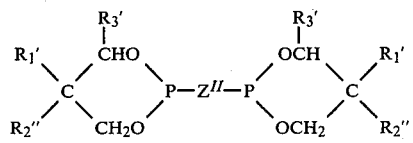 IV in which R$_1'$, R$_2''$, R$_3'$ and Z$^{II}$ are as defined above, is oxidized with a peroxy compound, preferably a per-acid.

Compounds of formula I in which X is sulphur may be prepared by addition of sulphur to compounds of formula III in conventional manner.

Compounds of formula II in which Z$^{II}$ is Z$_a^{II}$ may also be prepared by the reaction of 2 moles of a compound of formula V

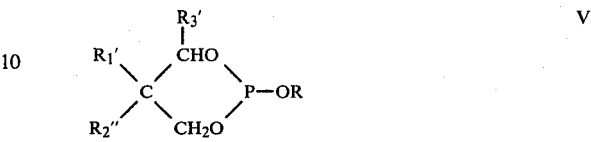 V in which R is ethyl or propyl,
or of a mixture of such compounds, with 1 mole of a compound of formula VI

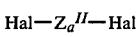

Hal—Z$_a^{II}$—Hal  VI in which —Z$_a^{II}$— is as defined above and Hal is chlorine or bromine, preferably bromine, the reaction being carried out in conventional manner.

The polymeric organic material containing the compound of formula I may in principle be any inflammable natural or synthetic organic polymer to which it is desired to impart flame-resistance, provided however that when Z in formula I is Z$_b$, i.e. when the compound of formula I is an O,O,O -triester of phosphoric or thiophosphoric acid, the organic polymer is not cellulose or a cellulose derivative.

Suitable organic polymers include polyolefins, for example polyethylene, polypropylene, ethylene-propylene copolymers, polystyrene and ABS resins; polyacrylonitrile; polymethyl methacrylate; polyesters for example polybutyleneterephthalate and particularly, polyethyleneterephthalate; unsaturated polyester resins; polyamides, for example nylon-6 and nylon-66; polyphenylene oxide; polycarbonate; polyurethanes and synethetic resins such as paints and varnishes. For the diphosphonic acid tetraesters, i.e. the compounds of formula I in which Z is Z$_a$, natural or regenerated cellulose and cellulose esters for example cellulose 2½-acetate or cellulose triacetate may also be used.

Preferably the flameproofed organic polymeric material of the invention is a thermoplastic, particularly a polyolefin, polyester, polyamide, polycarbonate or polyurethane containing a compound of formula I. More preferably it is a polyurethane or polyester, particularly polyethylene terephthalate.

The polymeric organic material may for example be in the form of bulk powder, granules or pellets suitable for further processing; in the form of fibres, film, foam or shaped articles formed e.g. by vacuum, compression or injection moulding; or in the form of woven or knitted textile fabrics or finished articles for example articles of clothing.

The polymeric organic material contains an effective flame-retarding amount of the compound of formula I, or, of course, of a mixture of one or more compounds of formula I, but this amount will vary within wide limits, depending upon the chemical nature and physical form of the material. In general, the material will contain from 0.1 to 40%, preferably from 0.5 to 20% by weight of the compound of formula I. For polyester, the content of compound of formula I is preferably 0.5 to 10, more preferably 1 to 5% by weight; for polyurethanes preferably 2.5 to 15%, more preferably 5 to 10% by weight; for polymethyl methacrylate preferably 5 to 20%, more preferably 8 to 15% by weight; for cellulose acetate preferably 0.5 to 10, more preferably 1 to 5% by weight.

The polymeric organic materials may contain other additives in addition to the compounds of formula I. These may be other types of flame-retardants, with which the compounds of formula I may have an additive or synergistic effect, or may be other types of additives conventionally used in such materials, for example heat and/or UV-stabilizers, antioxidants, dyes, pigments, optical brighteners, plasticizers, anti-static agents, etc. Such other additives may be surface-coated on the organic material, incorporated into the bulk of the material, or even co-polymerized with the corresponding monomer.

The invention also provides a process for the flameproofing of a polymeric organic material characterised by the incorporation of one or more compounds of formula I into the organic material before, during or after polymerisation, whereby when the compound of formula I is a phosphoric or thiophosphoric acid O,O,O-triester, the polymeric organic material is other than cellulose or a cellulose derivative.

The incorporation may be carried out by standard methods, depending upon the nature of the polymeric material. For example for certain types of polymers the compound of formula I may be mixed with the monomer or prepolymer and the mixture subjected for example to addition polymerization (e.g. for polymethyl methacrylate) or to polycondensation (e.g. for polyesters). The compound of formula I may also be blended with molten polymer for example polyester, before or during processing into shaped articles such as injection moulded articles, extruded film or fibres. The compound of formula I may also be added to a solution from which a fibre or film may be formed by evaporation of solvent or by precipitation in a suitable bath, for example for polyacrylonitrile, polymethyl methacrylate and, with the diphosphonic acid tetra-esters, for regenerated cellulose and cellulose acetate. Preferably, the compound of formula I, particularly the compound of formula $I_b'''$, is incorporated into polyethylene terephthalate by melt blending.

For the incorporation of a compound of formula I in polymeric organic materials, by melt blending or otherwise, it may be advantageous to add the compound of formula I in the form of a concentrate or master-batch composition containing for example 20 to 90%, preferably 30 to 60% by weight, of a compound of formula I. The remainder of the composition may comprise the same polymeric organic material as that which is to be flameproofed, optionally together with one or more other additives for example stabilizers, antioxidants, etc. Such concentrate or master-batch compositions also form part of the present invention.

Compounds of formula I give good flame-retardant effects at relatively low concentrations, particularly in polyesters, and are relatively chemically inert to polyesters under melt-processing conditions.

The following Examples in which all parts and percentages are by weight and temperatures are in degrees Centigrade, illustrate the invention.

Preparation of Compounds of Formula I

Each preparation of a compound which is believed to be novel constitutes an example of the invention and is assigned an example number. Preparations of compounds believed to be known are assigned a compound number C1, C2 etc.

EXAMPLE 1

35.6 Parts 5,5-dimethyl-2-ethoxy-1,3,2- dioxaphosphorinane, 18.8 parts 1,2-dibromoethane and 0.48 parts $NiCl_2.6H_2O$ are warmed to 130°–135° C. over 2 hours and finally stirred for 6 hours at this temperature. The mixture is cooled to room temperature, and the resulting thick suspension is diluted with 43 parts diethyl ether, filtered and washed with 20 parts diethyl ether, to give 8.5 parts of the compound of formula

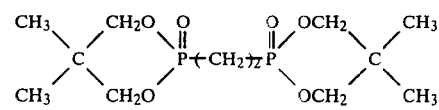

m.p. 219°–221° C.

EXAMPLES 2–5

Compounds C1, C2

In analogous manner, using appropriate dibromo compounds, compounds of formula

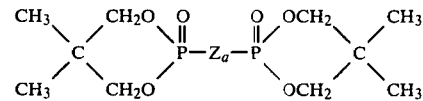

in which $Z_a$ is as shown in Table 1, are obtained.

TABLE 1

| Example or Compound No. | $Z_a$ | m.p. °C. |
| --- | --- | --- |
| C1 | $-CH_2-$ | 196–197 |
| 2 | $+CH_2\rightarrow_3$ | 171–175 |
| C2 | $+CH_2\rightarrow_4$ | 222–225 |
| 3 | $+CH_2\rightarrow_5$ | 134–136 |
| 4 | $+CH_2\rightarrow_6$ | 179–181 |
| 5 | $+CH_2\rightarrow_{10}$ | 169–171 |

Compound C3

88.5 Parts of the compound of formula

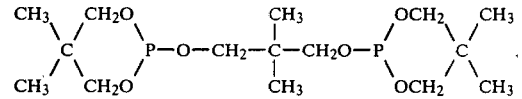

prepared by the method described in J.Org. Chem. 24 (1959), 630, is dissolved in 650 parts 1,2-dichloroethane. To this solution is added dropwise over 70 minutes 90.2 parts 3-chloroperbenzoic acid dissolved in 1125 parts 1,2-dichloroethane, cooling gently with ice to maintain the temperature at 20°–30° C. Finally, the reaction mixture is stirred 16 hours under reflux then cooled to 0°–5° for 30 minutes, when 3-chlorobenzoic acid precipitates. The mixture is filtered and the filtrate is tested to ensure that no peroxides are present, then shaken with 1000 parts 2% caustic soda solution, washed with water until neutral then dried over magnesium sulphate. After drying the solvent is distilled off, leaving 61 parts of a slightly resinous yellow product, which is then made into a paste with 70 parts diethyl ether, filtered after 1 hour and dried. The crude product (45 parts, m.p. 126°–128°) is recrystallised from 1680 parts carbon tetrachloride, giving 40 parts of the compound of formula

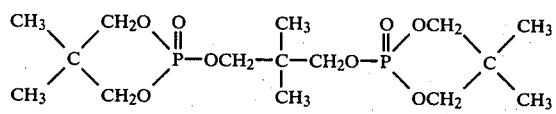

m.p. 128°–130°.

Compound C4–C7

In analogous manner, the following compounds may be prepared:

| Compound | Formula | m.p. |
|---|---|---|
| C5 | $\left[ \underset{CH_3}{\overset{CH_3}{>}}C\underset{CH_2O}{\overset{CH_2O}{<}}\overset{O}{\underset{}{P}}-OCH_2 \right]_4 C$ | 270° |
| C6 | $\left[ \underset{CH_3}{\overset{CH_3}{>}}C\underset{CH_2O}{\overset{CH_2O}{<}}\overset{O}{\underset{}{P}}-OCH_2 \right]_2 (CH_2Cl)_2$ | 184–7° |
| C7 | $\left[ \underset{CH_3}{\overset{CH_3}{>}}C\underset{CH_2O}{\overset{CH_2O}{<}}\overset{O}{\underset{}{P}}-OCH_2 \right]_3 C-C_2H_5$ | 187–9° |
| C8 | $\left[ \underset{CH_3}{\overset{CH_3}{>}}C\underset{CH_2O}{\overset{CH_2O}{<}}\overset{O}{\underset{}{P}}-OCH_2 \right]_2 C(CH_3)(C_6H_5)$ | 114° |
| C9 | $\left[ \underset{CH_3}{\overset{CH_3}{>}}C\underset{CH_2O}{\overset{CH_2O}{<}}\overset{O}{\underset{}{P}}-OCH_2 \right]_2 C(CH_2Br)_2$ | 171° |
| C10 | $\left[ \underset{n\text{-}C_3H_7}{\overset{CH_3}{>}}C\underset{CH_2O}{\overset{CH_2O}{<}}\overset{O}{\underset{}{P}}-OCH_2 \right]_2 C(CH_2Cl)_2$ | liq. |
| C11 | $\left[ \underset{CH_3}{\overset{CH_3}{>}}C\underset{CH_2O}{\overset{CH_2O}{<}}\overset{O}{\underset{}{P}}-OCH_2 \right]_3 CCH_3$ | 196–199° |

Compound C6

An alternative, preferred, method for the preparation of this compound is as follows:

136 Parts of pentaerythritol are dissolved in 100 parts of toluene, and 274.7 parts of phosphorus trichloride are added during 80 minutes at room temperature. After addition, the mixture is heated for 30 minutes to 40°–50° and subsequently for 2–3 hours to 65°–70°. During the reaction, hydrogen chloride is evolved. After addition of a further 140 parts of toluene, the solution is cooled to 25°–30°, and 142 parts of chlorine gas is added during 90 minutes at that temperature. Subsequently, the reaction mixture is added to a suspension of 208 parts of neopentyl glycol in 300 parts of toluene at 60°–70° C. within 15 minutes. The mixture is kept for 90 minutes at 60°–70°, followed by a reaction period of 150 minutes at 100°. During the reaction, hydrogen chloride is again evolved. The compound of formula C6 precipitates from the reaction mixture during cooling to room temperature. It is filtered off and dried. Melting point: 184°–187°.

In an analogous manner, the compound C10 can be prepared.

COMPOUNDS C12–C14

Compounds of formula

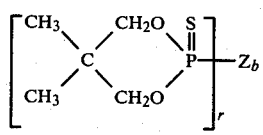

in which r and $Z_b$ are as given in Table 2, are prepared by reaction of the corresponding trivalent compounds with sulphur, suitably in an inert organic solvent.

TABLE 2

| Compound No. | r | $Z_b$ | m.p. °C. |
|---|---|---|---|
| C12 | 2 | $-OCH_2-\underset{CH_3}{\overset{CH_3}{\underset{|}{\overset{|}{C}}}}-CH_2O-$ | 164–165 |
| C13 | 4 | $C(CH_2O)_4$ | 240–242 |
| C14 | 2 | $-O-\text{C}_6\text{H}_4-O-$ | 204–206 |

Preparation of Flameproofed Polymers

EXAMPLE 6

400 Parts polyethylene terephthalate granules are mixed in a tumbler mixer with 12 parts of compound C3 at room temperature for 30 minutes. The mixture is then extruded in a laboratory extruder at 250° to 260°, and the granulate so obtained is dried for 16 hours at 140° and finally spun into fibres on a laboratory spinning apparatus at 285°. The fibres, which are drawn at a 1:4 draw ratio and have an identical thickness of 9.6 den, are woven into a fabric of weight 130 g/m², into which several rows of glass fibre are stitched. The finished fabric is subjected to the limiting oxygen index (LOI) test for flammability, as described by Fenimore and Martin (see Modern Plastics, November 1966), which indicates a very good flameproofing effect for Compound C3.

EXAMPLE 7

100 Parts polypropylene powder (Propathene GW 522M) are mixed well with 6 parts of Compound C2 and the mixture is melt blended on a roll mill at 165°–175° for 5 minutes. The resulting molten blend is press-moulded into 1 mm thick plates at 230° for 3 minutes. The plates are tested for flammability by the LOI test.

EXAMPLE 8

100 Parts of a commercial ABS powder are mixed with 6 parts of the compound of Example 4 on a laboratory roll mill at 160°–170° for 5 minutes, and finally pressed at 220° to 1 mm thick plates. The plates are tested for flammability by the LOI test.

EXAMPLE 9

100 Parts of a commercial polycarbonate powder are dried at 120° for 4 hours, then dry mixed in a shaker with 6 parts of the compound of Example 4. The mixture is extruded at 300° into a strand and chopped into granules. The granulate is further dried 4 hours at 120° and formed into 2 mm thick plates in an injection moulding machine. The plates are tested for flammability by the LOI test.

EXAMPLE 10

100 Parts of polyol (Voranol 4711, Dow Chemical Co.), 1.6 parts of a foam stabilizer, 0.12 parts amine catalyst (Desmorapid DB, Bayer AG), 0.18 parts stannous octoate and 4.8 parts water are stirred for 1 minute in a beaker at 1000–2000 rpm with 17.6 parts of Compound C3. To the mixture is added 58 parts of diisocyanate (Desmodur T80, Bayer AG), with stirring for 10 seconds. The foaming reaction mixture is poured into a mould, left for 2 hours at room temperature and finally cured for 2 hours at 60°. An even polyurethane foam of density 31 kg/m$^3$ is obtained. Test samples are cut from the foam and tested for flammability by the LOI test.

EXAMPLE 11

20 Parts cellulose acetate powder are dissolved by stirring in 80 parts acetone. To the solution is slowly added 0.40 parts of the finely ground compound of Example 3, and the mixture is stirred until the additive is evenly dispersed. The mixture is then poured onto a glass plate and spread out into a fine film. After evaporation of the acetone, the film is removed from the glass plate and dried in an oven at 85° for 30 minutes. The film is tested for flammability by the LOI test.

Examples 6–10 may be repeated using any of the compounds of Examples 1–5 and compounds C1–C7 and Example 11 may be repeated using any of the compounds of Examples 1, 2, 4 and 5 and compounds C1 and C2.

EXAMPLE 12

300 Parts of commercial polymethyl methacrylate granules (average molecular weight 120 000) are dried for 4 hours at 80° C. and 20 mmHg. The granules are dry-blended with 53 parts of compound C6, and the mixture is extrusion-moulded at 230° C. into a clear polymer/additive blend which is subsequently granulated. The granules obtained are dried for 6 hours at 80° C. and 20 mmHg and subsequently injection moulded into plates of 3 mm thickness. The plates are tested according to the oxygen index method (ASTM D 2863-77) where good values are achieved. In addition, the plates are self-extinguishing according to ASTM D 635.

EXAMPLE 13

Example 12 is repeated, except that 53 parts of compound C3 are used.

EXAMPLE 14

Example 12 is repeated except that 53 parts of compound C7 are used.

EXAMPLE 15

100 Parts of freshly distilled methyl methacrylate are mixed with 0.1 parts of dilauryl peroxide, 0.08 parts of azobisisobutyronitrile and 25 parts of compound C8.

The mixture is heated to the boil for a few minutes and subsequently poured between glass plates which are sealed with rubber and adhesive tape such that the distance between the plates is 3 mm. The glass plates are heated in a water bath for 16 hours at 50° C. and finally in an oven for 3 hours at 100° C. After removing the glass plates, polymer plates of 3 mm thickness are obtained which are tested as described in Example 12.

Example 12 may be repeated using compounds C9 and C11, and Example 15 using compound C10.

What is claimed is:

1. Flameproofed polymethyl methacrylate containing, as flameproofing agent, an effective amount of a compound or mixture of compounds of formula I

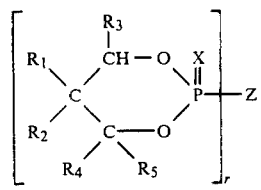

in which
- $R_1$ and $R_2$ are independently hydrogen, $C_{1-4}$alkyl or phenyl; or $R_1$ and $R_2$ together with the carbon atom to which they are attached form a cyclohexylidine or cyclohexenylidine ring,
- $R_3$ and $R_4$ are independently hydrogen or $C_{1-4}$alkyl,
- $R_5$ is hydrogen or methyl, provided that when $R_1$ and $R_2$ together with the carbon atom to which they are attached form a ring, then $R_3$, $R_4$ and $R_5$ are all hydrogen, Z is a group $Z_a'''$ or $Z_b$ where $Z_a'''$ is a $C_{1-10}$alkylene, $C_{6-8}$cycloalkylene, 2-butenylene or a group of the formula

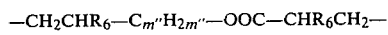

in which $R_6$ is hydrogen or methyl and $m''$ is 2, 3 or 4; and $Z_b$ is a group of the formula

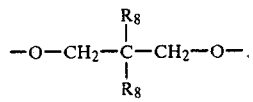

in which $R_8$ is $C_{1-4}$alkyl, phenyl, —CH$_2$Cl or —CH$_2$Br, or a group of the formula

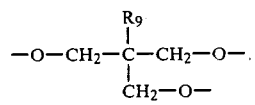

where $R_9$ is methyl or ethyl, or a group of the formula $$-O-CH_2-\underset{\underset{CH_2-O-}{|}}{\overset{\overset{CH_2-O-}{|}}{C}}-CH_2-O-,$$

X is oxygen when Z is $Z_a'''$ and oxygen or sulphur when Z is $Z_b$,
and r is 2 when Z is $Z_a'''$ and 2, 3 or 4 when Z is $Z_b$.

2. Flameproofed polymethyl methacrylate according to claim 2 in which, in formula I, Z is $Z_a'''$.

3. Flameproofed polymethyl methacrylate according to claim 1 in which, in formula I, Z is $Z_b$.

4. Flameproofed polymethyl methacrylate according to claim 1 in which, when r is 2, $Z_b$ is $Z_b'$ where $Z_b'$ is $$-O-CH_2-\underset{\underset{R_8'}{|}}{\overset{\overset{R_8'}{|}}{C}}-CH_2-O-$$

where $R_8'$ is $C_{1-4}$alkyl or phenyl.

5. Flameproofed polymethyl methacrylate according to claim 3 wherein $Z_b$ is $Z_b'$ where $Z_b'$ is $$-O-CH_2-\underset{\underset{R_8'}{|}}{\overset{\overset{R_8'}{|}}{C}}-CH_2-O-$$

where $R_8'$ is $C_{1-4}$alkyl or phenyl.

6. Flameproofed polymethyl methacrylate according to claim 5, containing as flameproofing agent, a compound of formula $I_b'$ $$\begin{array}{c} R_1' \quad CH_2O \quad X \qquad\qquad R_8' \qquad\qquad X \quad OCH_2 \quad R_1' \\ \diagdown / \quad \diagdown\| \qquad\qquad | \qquad\qquad \|/ \quad \diagdown / \\ C \qquad P-O-CH_2-C-CH_2-O-P \qquad C \\ / \diagdown \quad / \qquad\qquad | \qquad\qquad \diagdown \quad / \diagdown \\ R_2' \quad CH_2O \qquad\qquad R_8' \qquad\qquad OCH_2 \quad R_2' \end{array} \quad I_b'$$

in which
$R_1'$ and $R_2'$ are, independently, $C_{1-4}$alkyl or phenyl
X is oxygen or sulphur
and $R_8'$ is $C_{1-4}$alkyl or phenyl.

7. Flameproofed polymethyl methacrylate according to claim 6, containing, as flameproofing agent, a compound of formula $I_b''$ $$\begin{array}{c} R_1''' \quad CH_2O \quad O \qquad\qquad R_8'' \qquad\qquad O \quad OCH_2 \quad R_1''' \\ \diagdown / \quad \diagdown\| \qquad\qquad | \qquad\qquad \|/ \quad \diagdown / \\ C \qquad P-O-CH_2-C-CH_2-O-P \qquad C \\ / \diagdown \quad / \qquad\qquad | \qquad\qquad \diagdown \quad / \diagdown \\ R_2''' \quad CH_2O \qquad\qquad R_8'' \qquad\qquad OCH_2 \quad R_2''' \end{array} \quad I_b''$$

in which $R_1'''$ and $R_2'''$ are, independently, $C_{1-3}$alkyl and $R_8''$ is $C_{1-4}$alkyl.

8. Flameproofed polymethyl methacrylate according to claim 7 containing, as flameproofing agent, the compound of formula $I_b'''$ $$\begin{array}{c} CH_3 \quad CH_2O \quad O \qquad\qquad CH_3 \qquad\qquad O \quad OCH_2 \quad CH_3 \\ \diagdown / \quad \diagdown\| \qquad\qquad | \qquad\qquad \|/ \quad \diagdown / \\ C \qquad P-O-CH_2-C-CH_2-O-P \qquad C \\ / \diagdown \quad / \qquad\qquad | \qquad\qquad \diagdown \quad / \diagdown \\ CH_3 \quad CH_2O \qquad\qquad CH_3 \qquad\qquad OCH_2 \quad CH_3 \end{array} \quad I_b'''$$

9. Flameproofed polymethyl methacrylate according to claim 3 containing, as flameproofing agent, a compound of formula $$\left[ \begin{array}{c} R_1' \quad CH_2-O \quad X \\ \diagdown / \quad \diagdown \| \\ C \qquad P-O-CH_2 \\ / \diagdown \quad / \\ R_2' \quad CH_2-O \end{array} \right]_3 C-R_9$$

in which
$R_1'$ and $R_2'$ are, independently, $C_{1-4}$alkyl or phenyl
X is O or S
and $R_9$ is methyl or ethyl.

10. Flameproofed polymethyl methacrylate according to claim 10 containing, as flameproofing agent, a compound of formula $$\left[ \begin{array}{c} CH_3 \quad CH_2-O \quad O \\ \diagdown / \quad \diagdown \| \\ C \qquad P-O-CH_2 \\ / \diagdown \quad / \\ CH_3 \quad CH_2-O \end{array} \right]_3 C-R_9$$

in which $R_9$ is methyl or ethyl.

11. Flameproofed polymethyl methacrylate according to claim 1 containing from 5–20%, by weight, compound of formula I.

12. Flameproofed polymethyl methacrylate according to claim 11 containing 8–15%, by weight, compound of formula I.

13. Flameproofed polymethyl methacrylate according to claim 3 containing 8–15%, by weight, compound of formula I.

14. Flameproofed polymethyl methacrylate according to claim 6 containing 8–15%, by weight, compound of formula $I_b'$.

15. Flameproofed polymethyl methacrylate according to claim 8 containing 8–15%, by weight, compound of formula $I_b'''$.

16. A master batch composition comprising 10–80% by weight polymethyl methacrylate and 20 to 90% by weight of a compound or mixture of compounds of formula I $$\left[ \begin{array}{c} R_3 \\ | \\ R_1 \quad CH-O \quad X \\ \diagdown / \quad \diagdown \| \\ C \qquad P-Z \\ / \diagdown \quad / \\ R_2 \quad C-O \\ / \diagdown \\ R_4 \quad R_5 \end{array} \right]_r \quad I$$

in which
$R_1$ and $R_2$ are independently hydrogen, $C_{1-4}$alkyl or phenyl; or $R_1$ and $R_2$ together with the carbon atom to which they are attached form a cyclohexylidine or cyclohexenylidine ring,
$R_3$ and $R_4$ are independently hydrogen or $C_{1-4}$alkyl,
$R_5$ is hydrogen or methyl.
provided that when $R_1$ and $R_2$ together with the carbon atom to which they are attached form a ring, then $R_3$, $R_4$ and $R_5$ are all hydrogen,
Z is a group $Z_a'''$ or $Z_b$ where $Z_a'''$ is a $C_{1-10}$alkylene, $C_{6-8}$cycloalkylene, 2-butenylene or a group of the formula —CH$_2$CHR$_6$—C$_{m''}$H$_{2m''}$—OOC—CHR$_6$CH$_2$— in which R$_6$ is hydrogen or methyl and m'' is 2, 3 or 4; and Z$_b$ is a group of the formula

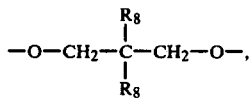

in which R$_8$ is C$_{1-4}$alkyl, phenyl, —CH$_2$Cl or —CH$_2$Br, or a group of the formula

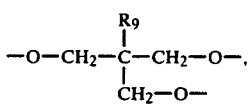

where R$_9$ is methyl or ethyl, or a group of the formula

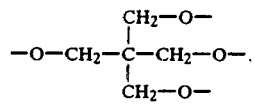

X is oxygen when Z is Z$_a'''$ and oxygen or sulphur when Z is Z$_b$, and r is 2 when Z is Z$_a'''$ and 2, 3 or 4 when Z is Z$_b$.

17. A master batch composition according to claim 16 comprising 10 to 80% by weight polymethyl methacrylate and 20 to 90% by weight of a compound or mixture of compounds of formula I wherein Z is Z$_b$.

18. A master batch composition according to claim 16 comprising 10 to 80% by weight polymethyl methacrylate and 20 to 90% by weight of a compound or mixture of compounds of formula I$_b'$

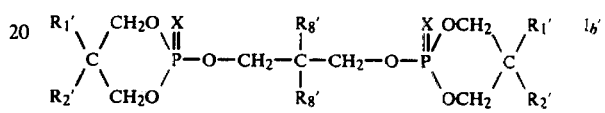

in which
R$_1'$ and R$_2'$ are, independently, C$_{1-4}$alkyl or phenyl
X is oxygen or sulphur
and R$_8'$ is C$_{1-4}$alkyl or phenyl.

* * * * *